United States Patent
Miller et al.

(10) Patent No.: US 10,729,387 B2
(45) Date of Patent: Aug. 4, 2020

(54) FREQUENCY-MULTIPLEXED SPEECH-SOUND STIMULI FOR HIERARCHICAL NEURAL CHARACTERIZATION OF SPEECH PROCESSING

(71) Applicant: THE REGENTS OF THE UNIVERSITY OF CALIFORNIA, Oakland, CA (US)

(72) Inventors: Lee Miller, Davis, CA (US); Bartlett Moore, IV, Houston, TX (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/406,047

(22) Filed: Jan. 13, 2017

(65) Prior Publication Data

US 2017/0196519 A1    Jul. 13, 2017

Related U.S. Application Data

(63) Continuation of application No. PCT/US2015/040629, filed on Jul. 15, 2015.
(Continued)

(51) Int. Cl.
| | | |
|---|---|---|
| *A61B 5/00* | (2006.01) | |
| *A61B 5/0484* | (2006.01) | |
| *A61B 5/0476* | (2006.01) | |

(52) U.S. Cl.
CPC ............ *A61B 5/741* (2013.01); *A61B 5/0476* (2013.01); *A61B 5/04845* (2013.01)

(58) Field of Classification Search
CPC ..... G06F 3/011; G06F 3/015; A61N 1/36036; A61N 1/36; A61N 1/08; A61N 1/36171;
(Continued)

(56) References Cited

U.S. PATENT DOCUMENTS

| | | |
|---|---|---|
| 4,275,744 A | 6/1981 | Thornton |
| 4,593,696 A | 6/1986 | Hochmair et al. |

(Continued)

FOREIGN PATENT DOCUMENTS

EP    2581038 A1    4/2013

OTHER PUBLICATIONS

Dau, T. et al., "Auditory brainstem responses with optimized chirp signals compensating basilarmembrane dispersion." J Acoust Soc Am 107(3): 1530-1540, Mar. 2000.
(Continued)

*Primary Examiner* — Deborah L Malamud
(74) *Attorney, Agent, or Firm* — Stoel Rives LLP

(57) ABSTRACT

A system and method for generating frequency-multiplexed synthetic sound-speech stimuli and for detecting and analyzing electrical brain activity of a subject in response to the stimuli. Frequency-multiplexing of speech copora and synthetic sounds helps the composite sound to blend into a single auditory object. The synthetic sounds are temporally aligned with the utterances of the speech corpus. Frequency multiplexing may include splitting the frequency axis into alternating bands of speech and synthetic sound to minimize the disruptive interaction between the speech and synthetic sounds along the basilar membrane and in their neural representations. The generated stimuli can be used with both traditional and advanced techniques to analyze electrical brain activity and provides a rapid, synoptic view into the functional health of the early auditory system, including how speech is processed at different levels and how these levels interact.

20 Claims, 5 Drawing Sheets

Related U.S. Application Data

(60) Provisional application No. 62/024,646, filed on Jul. 15, 2014.

(58) Field of Classification Search
CPC ............ A61N 1/36196; A61N 1/36034; H04R 25/606; H04R 25/505; H04R 25/305; H04R 25/353; A61B 5/0476; A61B 5/0482; A61B 5/04845; A61B 5/4064; A61B 2562/0204; A61B 5/0006; A61B 5/0042; A61B 5/121; A61B 5/4836; A61B 5/4848; A61B 5/486; A61B 5/7267; A61B 5/741; H04S 7/307
See application file for complete search history.

(56) References Cited

U.S. PATENT DOCUMENTS

| | | | |
|---|---|---|---|
| 5,230,037 | A | 7/1993 | Giustiniani et al. |
| 5,282,475 | A | 2/1994 | Urbach |
| 5,922,016 | A * | 7/1999 | Wagner ............... A61N 1/36036 128/898 |
| 5,983,129 | A | 11/1999 | Cowan |
| 6,053,739 | A | 4/2000 | Stewart |
| 6,067,467 | A | 5/2000 | John |
| 6,602,202 | B2 | 8/2003 | John |
| 8,712,514 | B2 | 4/2014 | Nicol |
| 2010/0030096 | A1 | 2/2010 | Bradley et al. |
| 2010/0208631 | A1* | 8/2010 | Zhang ..................... H04L 5/14 370/297 |
| 2012/0197153 | A1 | 8/2012 | Kraus et al. |

OTHER PUBLICATIONS

Galbraith, G. C. et al., "Intelligible speech encoded in the human brain stem frequencyfollowing response." Neuroreport 6(17): 2363-2367, Nov. 1995.
Elberling, C. et al., "A direct approach for the design of chirp stimuli used for the recording of auditory brainstem responses." J Acoust Soc Am 128(5): 2955-2964.4, Nov. 2010.
Hackley, S. A. et al., "Cross-modal selective attention effects on retinal, myogenic, brainstem, and cerebral evoked potentials." Psychophysiology 27(2): 195-208, Mar. 1990.
Billings, C. J. et al., "Predicting perception in noise using cortical auditory evoked potentials." J Assoc Res Otolaryngol 14(6): 891-903, online Sep. 13, 2013.
Tzovara, A. et al., "Progression of auditory discrimination based on neural decoding predicts awakening from coma." Brain 136(Pt 1): 81-89, Nov. 12, 2012.
Ding, N. et al., "Adaptive temporal encoding leads to a background-insensitive cortical representation of speech." J Neurosci 33(13): 5728-5735, Mar. 27, 2013.
Natus Medical Incorporated, "Bio-logic NavigatorPro", dowloaded from http://www.natus.com/index.cfm?page=products_clinical&crid=23, 1 page, 2017.
Skoe, Erika et al., "Auditory Brain Stem Response to Complex Sounds: A Tutorial", Ear & Hearing, vol. 31, No. 3, pp. 1-23, 2010.
Natus Medical Incorporated, "Navigator® Pro Master II", downloaded from http://www.natus.com/index.cfm?page=products_1&crid=29&locid=1001, 2017.
ISA/US, United States Patent and Trademark Office, International Search Report and Written Opinion dated Oct. 13, 2015, related PCT International Patent Application No. PCT/US2015/040629, pp. 1-8, with claims searched, pp. 9-13.
Walker, Kerry MM et al., "Multiplexed and robust representations of sound features in auditory cortex", J. Neurosci. 31(41), Oct. 12, 2011, pp. 14565-14576.

\* cited by examiner

US 10,729,387 B2

FREQUENCY-MULTIPLEXED SPEECH-SOUND STIMULI FOR HIERARCHICAL NEURAL CHARACTERIZATION OF SPEECH PROCESSING

CROSS-REFERENCE TO RELATED APPLICATIONS

This application is a 35 U.S.C. § 111(a) continuation of PCT international application number PCT/US2015/040629 filed on Jul. 15, 2015, incorporated herein by reference in its entirety, which claims priority to, and the benefit of, U.S. provisional patent application Ser. No. 62/024,646 filed on Jul. 15, 2014, incorporated herein by reference in its entirety. Priority is claimed to each of the foregoing applications.

The above-referenced PCT international application was published as PCT International Publication No. WO 2016/011189 on Jan. 21, 2016, which publication is incorporated herein by reference in its entirety.

STATEMENT REGARDING FEDERALLY SPONSORED RESEARCH OR DEVELOPMENT

This invention was made with Government support under DC008171, awarded by the National Institutes of Health. The Government has certain rights in the invention.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The present technology pertains generally to auditory stimuli and detecting electrophysiological signals in response to the stimuli, and more particularly to producing frequency-multiplexed chirp-speech stimuli that can be used with both traditional and advanced techniques to analyze electrical brain activity.

2. Background

Medical diagnosis and treatment of auditory system diseases and deficiencies have been advanced with an increased understanding of the integrated functions of the auditory system components. Generally, sounds presented at the eardrum are transmitted through the three bones of the middle ear to the oval window of the auditory inner ear called the cochlea. The movement of the oval window by the stapes bone pushes and pulls on the enclosed fluid of the cochlea creating compression pressure waves travelling approximately at the speed of sound in water. The motion of the fluid in the cochlear tubes also generates travelling waves along the length of the basilar membrane.

Sensory receptor cells, called hair cells, are positioned on an epithelial ridge on the basilar membrane called the organ of Corti. Motion of the basilar membrane of the cochlea activates the auditory receptor cells (hair cells) sitting on the membrane which send signals through the auditory nerve to the brainstem. The nerve signals activate more neurons and the auditory messages are sent to the midbrain, thalamus, and on to the auditory cortex of the temporal lobe of the cerebrum.

The cochlear travelling wave travels much slower than sound travels in water and peaks at frequency specific locations along the length of the basilar membrane. The basilar membrane is not uniform throughout its length and is relatively narrow but thick at the base and is relatively wide and thin at the apex of the cochlea. As a consequence of the structure, a cochlear travelling wave has a peak amplitude or height of displacement of the basilar membrane at a certain point along its length that is determined by the frequency of the sound that originally produced the motion of the cochlear fluid. High frequencies cause a peak wave near the narrow part of the membrane at the base and low frequencies produce their peaks toward the apex at the broad part of the membrane. The receptor cells on the basilar membrane may also be tuned to particular frequencies, so that each cell responds best to a sound of a given frequency.

The motion of the travelling wave of the basilar membrane is from the base up to the maximum point of displacement and then quickly fades. The latency of the traveling wave is quite short at the base, in the range of tens to hundreds of microseconds, but lengthens dramatically for peak displacements near the apex of the basilar membrane with latencies in the range of 10 ms or greater.

The traveling wave has been considered the fundamental mechanism for analysis of sounds in the cochlea since it was found that the traveling wave amplitude grows linearly with sound intensity and shows a broad peak near the resonant frequency location in the cochlea.

However, a time delay is observed from the initial auditory stimulus at the tympanic membrane and the neural activity produced in the auditory nerve or in the brain stem. It is also observed that the latency to the firing of auditory nerve fibers is comparatively shorter for fibers that are tuned to high frequencies and longer for fibers tuned to lower frequencies.

This latency is caused, in part, by frequency-dependent traveling wave delays. Because a traveling wave takes a period of time to reach from the base to the apical end of the cochlea, the corresponding receptor cells and fibers of the auditory nerve are not stimulated simultaneously. Consequently, synchronization between the nerve fibers is decreased due to the delays introduced by the traveling wave. The temporal dispersion or asynchrony of the collective output from the different neural elements results in a reduction of the amplitude of the corresponding compound neural response (e.g. ACAP or ABR).

The temporal asynchrony between the neural elements can be partially compensated for with a short auditory stimulus such as an upward chirp, where the higher frequencies are delayed relative to the lower frequencies. By aligning the arrival time of each frequency component of the stimulus, the chirp stimulus can shorten the latency and shift the waves. Essentially, the structure of the stimulus can influence the deflections of the basilar membrane and the corresponding timing of the stimulation of the hair cells of the basilar membrane and auditory nerve of the inner ear.

Auditory stimuli such as clicks, chirps or tone pulses have become part of several different procedures in the auditory field such as the auditory brain stem response (ABR), auditory compound action potential (ACAP), and the auditory steady-state response (ASSR). For example, hearing screening in newborns based on auditory brainstem response (ABR) is a well established method for the early detection of hearing impairment.

Several models have been developed that attempt to capture the major features of cochlear behavior. Nevertheless, there are many aspects of the human auditory system that are not fully understood. For example, it is not understood how different features of a sound, such as frequency, intensity, or onset and offset that are carried to higher brain centers separately through parallel nerve pathways are interpreted by the cerebral cortex.

Speech is perhaps the most important stimulus that humans encounter in their daily lives. Unfortunately, certain populations have difficulty understanding speech, particularly in noisy conditions, including children with language-based learning problems and users of cochlear-implant/hearing-aids. Even in the hearing impaired, much of this difficulty stems not from problems in the ear itself, but from how each individual's brain processes the speech sounds.

Considering its importance, audiology clinics devote little effort to the neural processing of continuous speech from the ear to auditory cortex. Currently there is no way to rapidly and reliably assess the integrated functioning of the auditory system from brainstem to cortex. For this profound, global health problem, no clinical assessment tool exists. Accordingly, there is a need for devices and methods that will allow the diagnosis, treatment and study of human hearing.

BRIEF SUMMARY

The present technology provides synthetic sound-speech stimuli and a method for creating sound-speech stimuli that can be used with both traditional and advanced techniques to analyze electrical brain activity. The synthetic sound-speech stimuli used in conjunction with suitable diagnostic systems can provide a wide variety of assessments as well as experimental procedures for medical practitioners and researchers. For example, it will provide a rapid, synoptic view into the functional health of the early auditory system, including how speech is processed at different levels and how these levels interact. It will give clinicians a quantum leap in diagnostic power, enabling them to customize treatment and/or hearing device algorithms to a particular individual.

The synthetic sound-speech stimuli can provide a simultaneous assessment of multiple levels of the auditory system with realistic stimuli such as speech. Many different traditional techniques could be used to assess each level independently. However these methods generally: 1) would take too long to implement in the clinic and therefore would neither be adopted by clinicians nor reimbursed by insurers; 2) would lack the power to analyze relations among different levels of processing; and 3) do not even use actual speech or similar complex sounds, and therefore may not be representative of speech perception in everyday experience. One of the greatest challenges in the hearing loss industry is assessing how patients will perform in real environments, and to explain the variability among patients. This technology enables such an assessment.

The synthetic sound-speech stimuli can be adapted to different procedures through the selection of the elements and structure of the stimuli. Thus, the selection of the procedure can influence the selection of the characteristics of the elements.

In the typical case, the synthetic sound-speech stimuli will be created with speech stimuli that are frequency multiplexed with one or more sound stimuli. Any speech stimuli can be used, from brief isolated utterances to fully continuous running speech. In addition, one or more speech signals may be used simultaneously.

The speech stimuli are normally a common clinical speech corpus. A speech corpus is a database of speech audio files of specific utterances (e.g. words or sentences) that are naturally spoken by an actor. The speech corpus can also be custom tailored to a particular patient so that the speech corpus is a familiar voice, enabling the use of familiar voices in standard assessments, such as using a mother's own voice for infant screening.

The pitch of the speech corpus is preferably flattened to a constant value to ensure that the phase is consistent within the utterances. However, pitch flattening may be optional in some embodiments.

Next, a synthetic sound or sounds are selected. Typical sounds are chirps, clicks or brief noise bursts, with chirps being particularly preferred. The conventional click stimulus is a 100 µs pulse that has a frequency range from approximately 100 Hz to approximately 10,000 Hz. There are also many different types of chirps with a variety of characteristics that have been designed. These chirps have frequency components with timing that maximizes the response of the cochlea and increases the synchrony of neural firings of the auditory pathway.

The selected synthetic sound trains are spectrally multiplexed and temporally aligned with the modified speech corpus. That is, the frequency axis is split into alternating bands (e.g. approximately 0.5 to 1 octave wide) of speech and synthetic sound (e.g. chirp).

The frequency-multiplexed synthetic sound-speech stimulus can then be used in the context of the selected diagnostic system on a patient or test subject. In addition, libraries of frequency-multiplexed synthetic sound-speech stimuli can be developed that have stimuli with incremental variations in the sound and speech components.

There are many possible measurement or analysis techniques that can be adapted for use with the configurable synthetic sound-speech stimuli. For example, in one embodiment, the generated stimuli can be used to help determine the cause of hearing/language/selective attention impairment in an individual, and/or classification of individuals into sub-types of auditory processing disorders. A simple illustration is a "cortical hearing test" where the fidelity of speech processing by the higher brain is evaluated with the proposed stimulus, for instance in different EEG frequency ranges. Ultimately this would be compared to a normal hearing standard, as with typical clinical hearing tests. Such tests may incorporate traditional neural measures of auditory, linguistic and cognitive processing including but not limited to the mismatch negativity (MMN), N400, and P300. Such tests could also be used with varying pitch in non-tonal languages or in tonal languages (e.g. Mandarin) to assess the behavioral and/or brain response of 'tracking' changing pitch, whether it conveys linguistic or paralinguistic (e.g. prosodic) cues.

In another embodiment, the frequency-multiplexed synthetic sound-speech stimuli can be used to assess auditory function in a frequency-specific manner by using separate chirps limited to certain frequency bands rather than single chirps spanning the entire audible range.

The methods can be used to help audiologists fit hearing aids with greater accuracy, adaptively in real time, with lower return rates and increased customer satisfaction. The stimuli can be adapted to measure listening effort, which is a significant burden for the hearing impaired particularly in real-world acoustic situations. It can also be used to measure neural correlates of acceptable noise levels (ANL), currently one of the only reliable predictors of hearing aid use.

The methods can be used on a one-time or longitudinal basis with or without hearing impairment, e.g. for tracking degraded speech processing during normal aging, or for screening and early diagnosis of peripheral impairment and central auditory processing/language-based disorders in infants and children (e.g. wave V-SN10 or wave V-Vn deflection). The methods can be used in eliciting otoacoustic emissions (OAEs), e.g. in assessing auditory neuropathy.

The stimuli can also be used to enhance procedures that predict coma prognosis such as coma awakening by detecting auditory processing of pure tones or diagnose neuropsychiatric conditions characterized by altered auditory or linguistic function, such as schizophrenia.

The methods can be used in healthy or patient populations in brain-machine interfaces to provide feedback or to control a device, for instance changing settings for automatic speech recognition.

The stimuli characteristics can be altered in a controlled manner and used to assess specific component perceptual and neural processing abilities that comprise speech processing (for example fidelity of temporal processing wherein one may deliberately disrupt the chirp timing).

The stimuli and methods can be incorporated in broader behavioral and/or neural testing suites for perceptual and cognitive function (attention, working memory etc.). It can also be used to assess functional hemispheric laterality or asymmetry of auditory and cognitive processing.

The methods can be adapted for the use of music or any other complex sound containing transient events, whether periodic or non-periodic, where transient events could be frequency-multiplexed with a synthetic sound as described herein.

The stimuli can also be used with procedures to localize neural processing, either healthy or impaired, to specific anatomical structures, e.g. with EEG/MEG source localization techniques such as beam forming or through a combination with functional magnetic resonance imaging.

The multiplexing methods can also be used for processing sounds (with or without neural recording) such that they are heard better, more clearly or with greater comprehension by alternately multiplexing different sound streams to reduce acoustic masking. This could apply to the hearing impaired or to healthy listeners in acoustically adverse environments, e.g. public spaces, industry, or military (as in noisy land-based or air-based vehicles, or on the battlefield).

It is also possible to identify or "tag" one sound versus other sounds based on their neural processing, either primarily in response to the multiplexed synthetic sound or in combination with other acoustic attributes at multiple time scales. For instance two simultaneous talkers may be distinguished by different chirp rate (e.g. 38 Hz vs 43 Hz) and/or different speaking rate as reflected in the amplitude envelope, (e.g. 3 Hz vs 5 Hz).

The methods can also be adapted to be integrated into the function of portable and wearable consumer devices such as phones, tablets, watches, earphones, and headsets for processing audio signals (as in cellular/wireless voice communication) and for device command, control, and brain-device/device-brain feedback.

According to one aspect of the technology, an auditory stimulus is provided that has a speech component that is "frequency-multiplexed" with a synthetic sound that evokes strong early auditory system (including brainstem) responses, such as a chirp train.

A further aspect of the technology is to provide auditory stimuli that use synthetic sounds that are non-speech sounds selected from the group consisting of chirps, clicks, tones or tone-complexes, and amplitude-modulated noise bursts.

Another aspect of the technology is to provide a method for producing auditory stimuli where a speech component is frequency-multiplexed with a synthetic sound by splitting the frequency axis into alternating bands of speech and synthetic sound to minimize disruptive interaction between the speech and synthetic sounds along the basilar membrane and in their neural representations.

According to a further aspect of the technology, a method for analyzing electrical brain activity with frequency-multiplexed synthetic sound-speech stimuli is provided where the method is performed by executing programming on at least one computer processor with the programming residing on a non-transitory medium readable by the computer processor.

Further objects and aspects of the technology will be brought out in the following portions of the specification, wherein the detailed description is for the purpose of fully disclosing preferred embodiments of the technology without placing limitations thereon.

BRIEF DESCRIPTION OF THE SEVERAL
VIEWS OF THE DRAWINGS

The technology described herein will be more fully understood by reference to the following drawings which are for illustrative purposes only:

DETAILED DESCRIPTION

Referring more specifically to the drawings, for illustrative purposes, embodiments of the apparatus and methods for frequency-multiplexed synthetic sound-speech stimuli and analyzing electrical brain activity are generally shown. Several embodiments of the technology are described generally in FIG. 1 through FIG. 10 to illustrate the methods. It will be appreciated that the methods may vary as to the specific steps and sequence and the apparatus may vary as to structural details without departing from the basic concepts as disclosed herein. The method steps are merely exemplary of the order that these steps may occur. The steps may occur in any order that is desired, such that it still performs the goals of the claimed technology.

Figure 1:
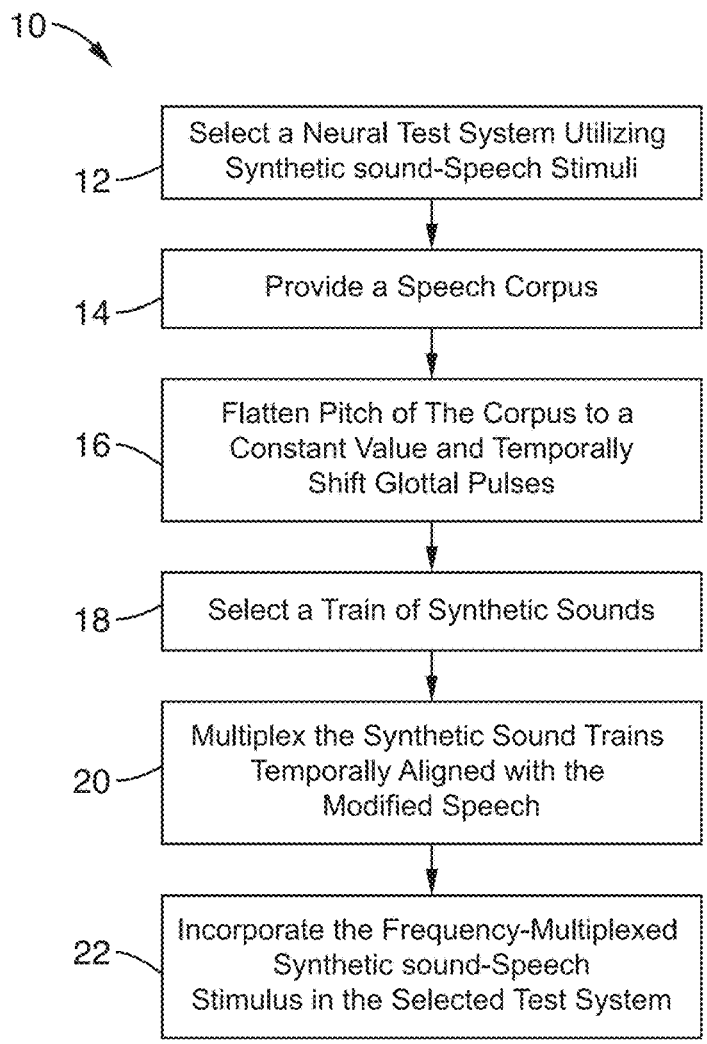
FIG. 1 is a schematic flow diagram of a method for producing frequency-multiplexed synthetic sound-speech stimuli for analyzing electrical brain activity according to one embodiment of the technology.

Referring now to FIG. 1, a method 10 for producing and using frequency-multiplexed synthetic sound-speech stimuli is depicted schematically. At block 12 of FIG. 1, the test system that will utilize the synthetic sound-speech stimuli is selected. The characteristics of the stimuli that can be produced with the methods can be optimized and adapted to be used with both traditional and advanced techniques to analyze electrical brain activity. The nature of the detection apparatus and manner in which the electrophysiological signals that occur in response to the stimuli are detected may influence the configuration of the synthetic sound-speech stimuli that is developed.

Once the test system, stimuli and response detection system are selected, the synthetic sound-speech stimuli configuration can be determined. Table 1 provides a sample of frequency-multiplexed synthetic sound-speech stimuli generating MATLAB and Praat Code for generating stimuli according to one embodiment of the technology described herein.

At block 14 of FIG. 1, at least one speech corpus is provided. A speech corpus is a database of speech audio files, usually read by an actor with text transcriptions, or may be composed of spontaneous speech or narratives. The speech can be produced by a live speaker or it can be synthesized, for example with text-to-speech algorithms. Any speech stimuli can be used at block 14, from brief isolated utterances to fully continuous running speech. For instance, the method could be used on all common clinical speech corpuses such as HINT, QuickSIN or Synthetic Sentence Identification test. Speech stimuli based on the Harvard/IEEE (1969) speech corpus, a large set of low-context sentences that are thoroughly normed and widely used, are particularly suitable. In addition, one or more speech signals may be used simultaneously. The method can also be used in real time on streaming media or offline, after sounds are recorded.

At block 16 of FIG. 1, the pitch of the sentences that are naturally spoken by an actor of the speech corpus is optionally flattened to a constant value or level. In one embodiment, the pitch constant is approximately 82 Hz, which is approximately the low limit of a male voice. However any value in the natural range of human pitch perception is acceptable.

The pitch is also flattened to a constant to ensure that voicing (glottal pulse) phase is consistent within utterances. This pitch flattening, a corollary to the primary technology of frequency-multiplexing, is not absolutely required but makes subsequent analysis more straightforward and robust. In one embodiment, the times of pitch-flattened glottal pulses are shifted by up to half a pitch period (+/−6 ms for a pitch of 82 Hz), to keep voicing phase consistent within and across speech utterances.

A synthetic sound or sounds that preferably evoke strong early auditory system (including brainstem) responses, such as a chirp train are then selected at block 18 of FIG. 1. A standard chirp can be selected at block 18, or the chirp can be customized to the individual listener. The sound intensity and other characteristics of the chirp can also be customized.

Other non-speech sounds such as clicks, tones or tone-complexes, or amplitude-modulated noise bursts could be used in the alternative, but chirps have been shown to be optimal and are particularly preferred. Additionally, if the pitch were not flattened, the chirps would not be isochronous and would track the changing pitch instead.

In Example 1, the chirp train that was selected was an isochronous 41 Hz series of "cochlear chirps." These chirps compensate for the traveling wave velocity in the basilar membrane, resulting in a more synchronized neural response and larger auditory brainstem response (ABR) as well as a potentially more robust middle latency responses (MLR) and long latency responses (LLR).

The selected train of synthetic sounds is frequency-multiplexed with the modified speech corpus at block 20 of FIG. 1 to produce synthetic sound-speech stimuli with characteristics determined in part by the speech and synthetic sound components and the configuration of the combination.

In one embodiment, the multiplexing at block 20 includes temporally aligning the synthetic sound trains with the modified speech. The frequency axis is split into alternating bands of speech and synthetic sound (chirps) to minimize disruptive interaction between the two sounds along the basilar membrane and in their neural representations, while ensuring that i) enough speech signal remains across all frequencies to be potentially intelligible, and ii) the speech perceptually blends with and is not perceptually masked by the synthetic sounds. The number of bands, width of bands, and relative intensity between speech and synthetic sound (chirp) may be adjusted to suit different purposes. The bands may be stable for a given sound or may vary over time, for instance to track the spectral peaks of formants. That is, the frequency bands that are multiplexed between speech and synthetic sound may be dynamic rather than stable over time. For instance, the spectral centers and widths of formant peaks during voiced epochs could define the centers and widths of the multiplexed chirp frequency bands, whereas speech energy would occupy all other bands (and all frequencies during unvoiced epochs).

In Example 1, these chirp trains only occur during voiced epochs of speech, and are temporally aligned with every other glottal pulse (except for near voicing onset, where the second chirp is omitted to allow cleaner assessment of an ABR and especially MLR). This alignment of the synthetic energy with glottal pulse energy, a corollary to the primary technology of frequency-multiplexing, helps the composite sound to blend into a single auditory object—an important attribute for higher level perception and cognition. Following the same principle, synthetic sounds can be temporally aligned with acoustic speech attributes in addition to glottal pulses, such as consonant plosives. Depending on the acoustics of the speech elements that are co-temporal with the synthetic sound, different synthetic sounds may be used at different moments, for example chirps during glottal pulses and noise bursts during plosives. The chirp-speech stimuli may therefore sound somewhat harsh or robotic but are largely natural and readily intelligible.

At block 22 of FIG. 1, the synthetic sound-speech stimuli that are produced at block 20 can be incorporated into the test system that was selected at block 12. It can be seen that the synthetic sound-speech stimuli that are produced can be used immediately on a test subject or they can be recorded and saved in a library of stimuli. The searchable library can include groups of synthetic sound-speech stimuli that have incremental variations in the characteristics of the components and multiplexed structure. Physiological responses to different synthetic sound-speech stimuli can also be compared and analyzed. A searchable library of a wide variety of different synthetic sound-speech stimuli combinations at block 22 will give the system greater sensitivity and accuracy.

Typically, the synthetic sound-speech stimulus is presented to at least one outer ear of a subject. However, the stimulus could be presented to both ears, with the same or different speech signal in each ear. For frequency-specific assessment of auditory function, the chirps could be presented not as single chirps that span multiple audible frequency bands, but as separate chirp segments occupying only certain frequency bands. Subjects need not perform a task. For example the subjects can either listen attentively to the speech stimulus or can watch a silent movie to maintain general arousal instead.

Furthermore, the generated stimulus need not be delivered acoustically, but could also apply to electrical transmission of speech signals, as with cochlear implants (CI). Minor differences would apply since there is no basilar membrane traveling wave delay in a cochlear implant. However the frequency-multiplexing of clicks or implant-electrode-multiplexing or other synthetic signals with speech would be useful in analogous ways to those described herein.

Cochlear implants add an additional means of recording early auditory potentials via the device itself, known generally as telemetry or telemetry-evoked compound action potential recording (of the auditory nerve), e.g. Advanced Bionics' Neural Response Imaging. The methods can also be used with CI telemetry to improve fitting and sound perception, upon implantation and over time, in analogous ways to those described for hearing aids.

While the primary technological advancement described herein includes methods for creating speech stimuli, their utility comes through analyzing neural responses to the stimuli with measuring and recording techniques including electroencephalography EEG, magnetoencephalography MEG, electrocorticography ECoG, and cochlear implant telemetry. For instance, EEG can be recorded with typical clinical systems, i.e. a small number of electrodes (e.g. 1-6, including one near vertex) with sampling rate high enough to capture the ABR (e.g. 16 kHz).

There are many possible measurement or analysis techniques that can be adapted for use with the configurable synthetic sound-speech stimuli. To illustrate the variety of applications of the configurable synthetic sound-speech stimuli, several conventional assessment procedures were adapted for use with synthetic sound-speech stimuli.

The following synthetic sound-speech stimuli methods can be illustrated in the following examples:

(1) Auditory brainstem response (ABR) following the presentation of chirp synthetic sounds. The ABR assesses neural responses from the auditory nerve through the inferior colliculus (IC), the most important integrative structure in the ascending auditory system. For instance wave V (or the V-Vn complex), the largest component, arises from the input to IC and its further processing, and therefore yields the single best measure of "bottom-up" auditory processing—how well sounds have been encoded into brain signals in the first place.

(2) MLR and Auditory steady state response (ASSR) at approximately 40 Hz. The ASSR shares generators with the middle latency response, and therefore characterizes sensory representations from thalamus to early, likely-primary auditory cortex—how well speech information is passed from lower to higher levels in the auditory system.

(3) Long-latency responses (LLRs) such as P1/N1/P2 waves and the Temporal Response Function (TRF) for the speech envelope. The TRF is a linear kernel derived by reverse correlation between the low frequency (<40 Hz, e.g. 1-8 Hz) EEG/MEG and the speech amplitude envelope. LLRs measure the strength of speech representation in non-primary auditory cortex—how well speech information is represented in the higher auditory brain. Note the presence of synthetic sound trains (chirps), being co-temporal with epochs of high speech power (voicing), may yield more robust LLRs than speech alone.

(4) Alpha (8 Hz-12 Hz) power and laterality, over the occipitoparietal scalp, e.g. as an indicator of selective attention. This is a prime example of how the stimulus can be used in conjunction with high-level perceptual and cognitive measures.

In addition to these basic time or frequency measures, one can analyze time-frequency measures such as event-related spectral perturbation (ERSP, e.g. as implemented in EEGLAB), or trial-to-trial phase consistency. One can also analyze relationships among levels, from simple correlations between levels across time blocks (e.g. single-trial or 1 min running average of ABR wave V, ASSR power, and TRF amplitude) to more sophisticated cross-frequency, cross-time, and/or cross-location coupling. For instance, functional coupling of activity among different cortical brain areas has been shown to index numerous perceptual and cognitive functions. The present technology enables, for the first time, a vast array of functional measures to span the ascending auditory system as well. The mathematical or computational techniques to assess functional connectivity are numerous and include but are not limited to correlation/covariance and coherence-based methods, autoregressive-based methods (Granger causality), dynamic causal models, and analyses of network topology. Such methods can be applied in the time, spatial, and frequency domains (e.g. Partial Directed Coherence). Different states of speech processing or of functional connectivity can also be identified and classified with machine learning approaches to neural response patterns and data mining algorithms (e.g. blind source separation methods such as Independent Component Analysis).

The technology described herein may be better understood with reference to the accompanying examples, which are intended for purposes of illustration only and should not be construed as in any sense limiting the scope of the technology described herein as defined in the claims appended hereto.

Example 1

In order to demonstrate the technology, a "Functionally Integrated Speech Hierarchy" (FISH) assessment comprising a new speech stimulus corpus and advanced EEG analysis procedures was performed. For this illustration, 16 subjects with normal hearing and one subject with impaired hearing were recruited. EEG was acquired at 16 kHz with 20 channels distributed across the scalp while subjects listened attentively or watched a silent movie.

Sound attributes and analyses were jointly designed on mathematical and physiological principles to provide simultaneous but independent characterization of different levels of the ascending auditory system. The FISH assessment included multiple simultaneous measurements of the following:

1) Auditory brainstem response (ABR) to the first, last, and/or all chirps in each train. The ABR assesses neural responses from the auditory nerve through the inferior colliculus (IC), the most important integrative structure in the ascending auditory system. Wave V, the largest component, arises from the input to IC, and therefore gives the single best measure of "bottom-up" auditory processing. See FIG. 5.

2) Middle Latency Response (MLR) and Auditory Steady State Response (ASSR) at 41 Hz. The ASSR shares generators with the middle latency response, and therefore characterizes sensory representations from thalamus to early, likely-primary auditory cortex.

3) Temporal Response Function (TRF) for the speech envelope. The TRF is a linear kernel derived by reverse correlation between the low frequency (<40 Hz) EEG and the speech envelope. LLR's measure the strength of speech representation in non-primary auditory cortex.

4) Alpha (8 Hz-12 Hz) power and laterality, over the occipito-parietal scalp, e.g. as an indicator of selective attention.

In addition to these basic measures, relationships among levels were analyzed, from simple correlations between levels across time blocks (e.g. 5 min running average of ABR wave V, ASSR power, and TRF amplitude) to more sophisticated cross-frequency, cross-time, and/or cross-location coupling.

Figure 2:
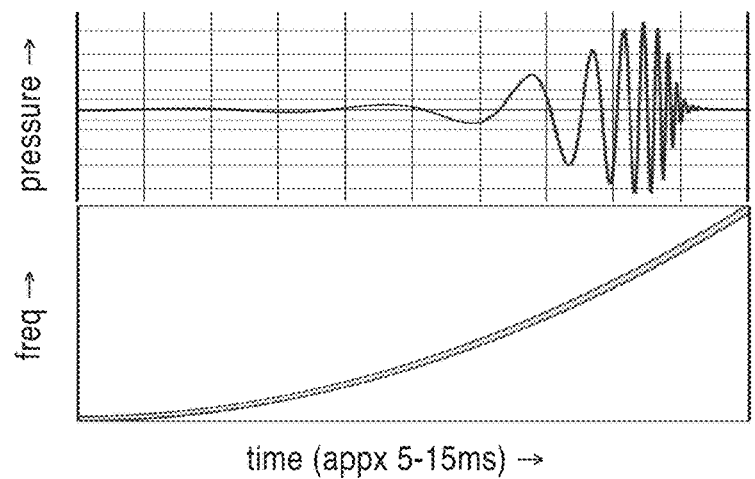
FIG. 2 is a time waveform and spectrogram (time-frequency plot) of a single chip according to an embodiment of the technology.

A frequency-multiplexed chirp-speech stimulus was generated for the FISH assessment. The stimuli were based on the Harvard/IEEE (1969) speech corpus, a large set of low-context sentences that are widely used. The sentences were naturally spoken by an actor and the pitch was then flattened to a constant 82 Hz (the approximate lower limit of a male voice) and the glottal pulses were shifted (by +/−6 ms) to keep voicing phase consistent within utterances. FIG. 2 depicts a time waveform and spectrogram (time-frequency plot) of a single chirp that was part of the chirp train.

Figure 3:
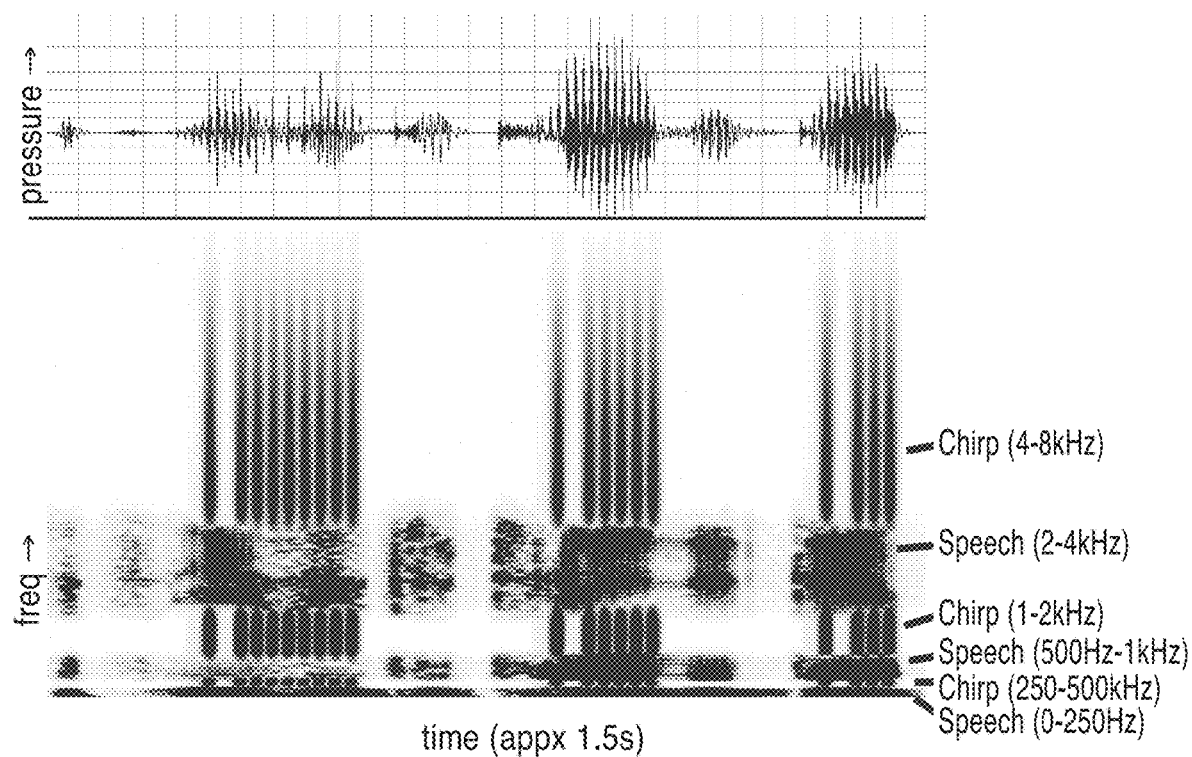
FIG. 3 shows how speech is frequency-multiplexed with chirp trains aligned to voicing according to an embodiment of the technology.
Figure 4:
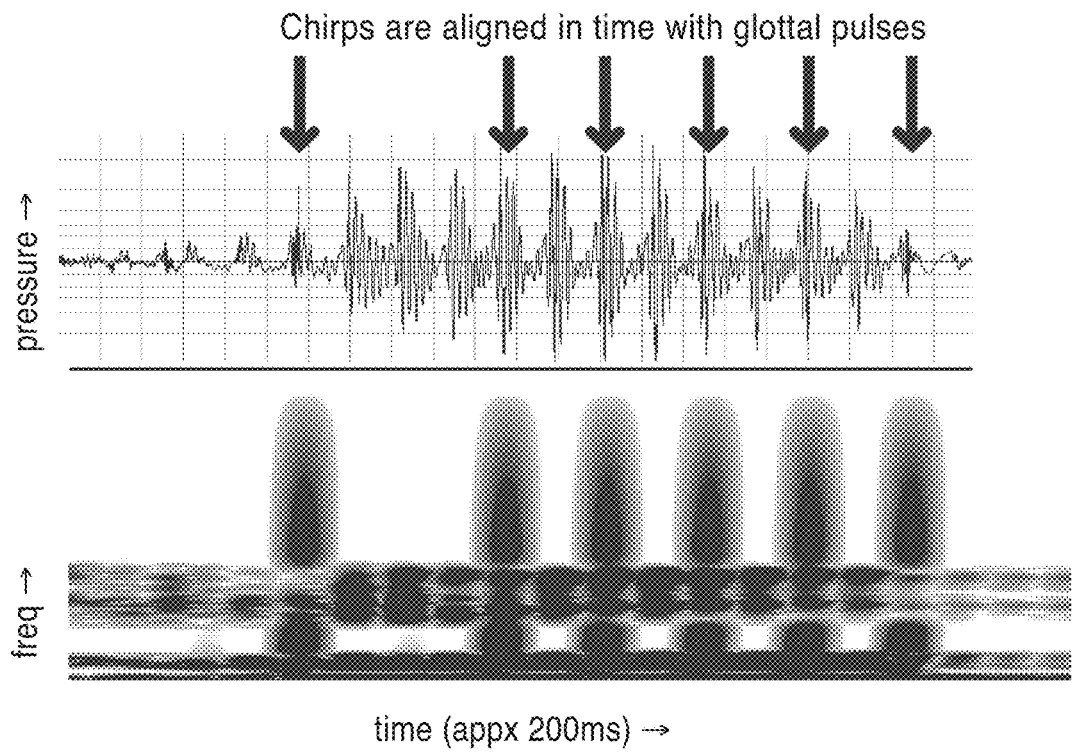
FIG. 4 shows chirps aligned in time with glottal pulses acceding to an embodiment of the technology.

Next, the speech was "spectrally multiplexed" with a chirp train. That is, the frequency axis was split into alternating bands approximately 1 octave wide of speech and chirps in this illustration. The chirp train was an isochronous series of 41 Hz "cochlear chirps," which compensate for the traveling wave velocity in the basilar membrane, resulting in a more synchronized neural response and larger auditory brainstem response (ABR). FIG. 3 illustrates how speech is frequency-multiplexed with chirp trains that are aligned to voicing. These trains only occur during voiced epochs of speech and are temporally aligned with every other glottal pulse (except for near voicing onset, where the second chirp is dropped to allow cleaner assessment of an ABR and MLR). FIG. 4 shows chirps aligned in time with glottal pulses. The FISH speech stimuli therefore sound somewhat harsh or robotic but were found to be largely natural and readily intelligible.

Example 2

To further demonstrate the technology, neural responses to the same frequency-multiplexed chirp-speech stimuli were performed from a group of 17 subjects. In this example, the chirp train component was an isochronous 41 Hz series of "cochlear chirps". These chirps compensate for the traveling wave velocity in the basilar membrane, resulting in a more synchronized neural response and larger auditory brainstem response (ABR) as well as a potentially more robust middle latency responses (MLR) and long latency responses (LLR).

Figure 5:
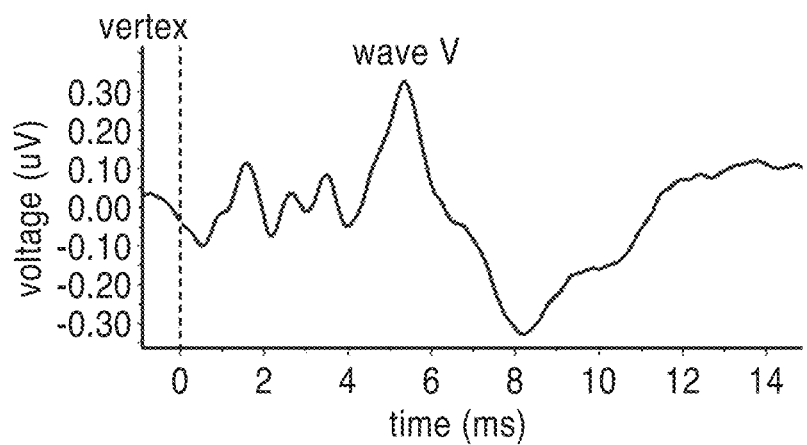
FIG. 5 is a graph showing auditory brainstem response (ABR).
Figure 6:
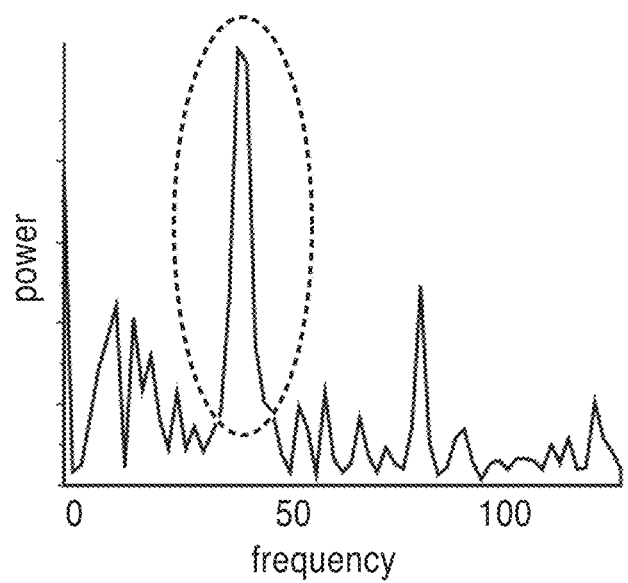
FIG. 6 is a graph that shows an auditory steady state response (ASSR) at 41 Hz.
Figure 7:
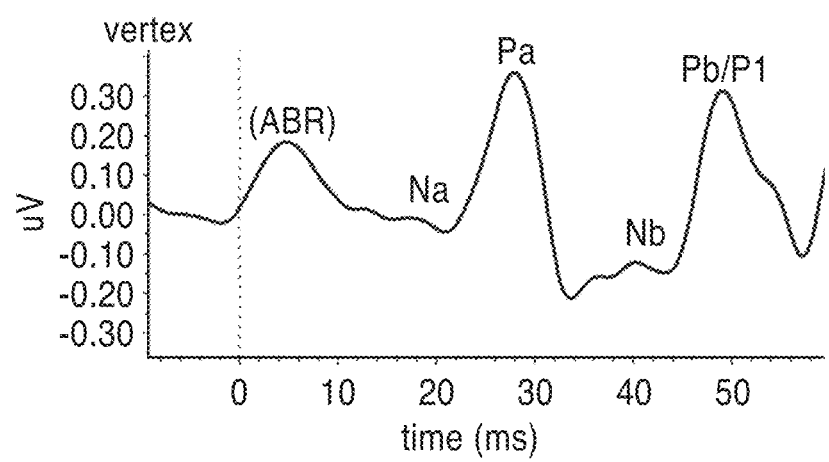
FIG. 7 is a graph that shows a middle-latency response (MLR).
Figure 8:
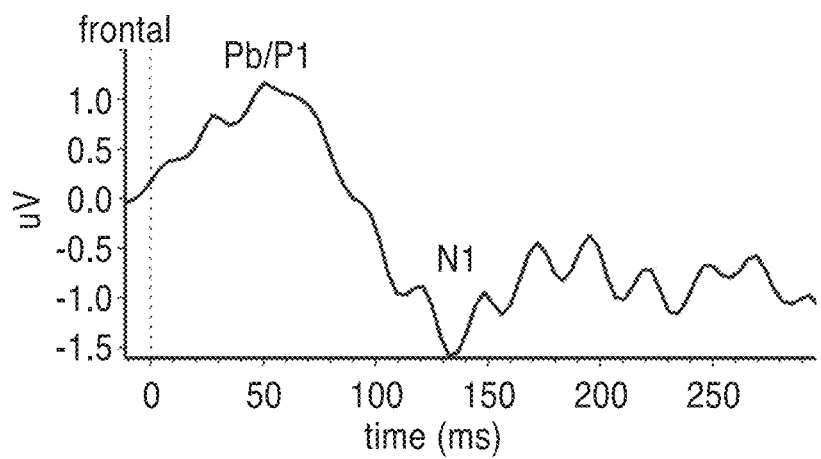
FIG. 8 is a graph that shows a long-latency response (LLR).
Figure 9:
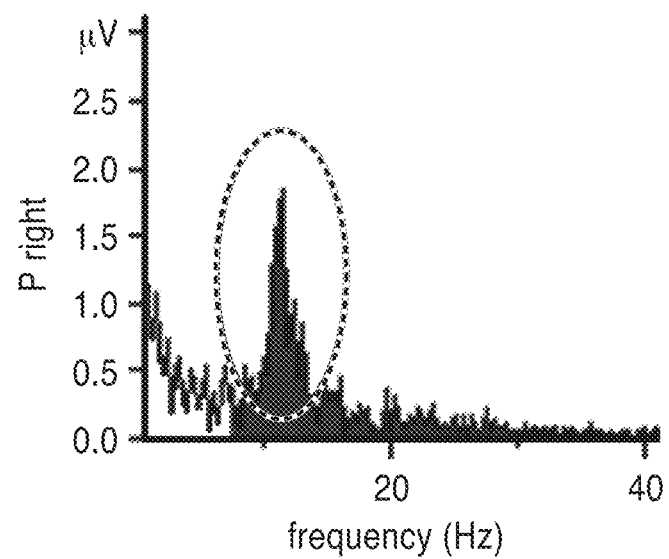
FIG. 9 is a graph that shows alpha power at 12 Hz over the parietal lobe.

FIG. 5 is a graph showing auditory brainstem response (ABR) of a test subject that was presented the frequency-multiplexed chirp-speech stimulus of Example 1. FIG. 6 is a graph of the auditory steady state response (ASSR). FIG. 7 shows middle-latency response (MLR) and FIG. 8 shows the long-latency response (LLR). FIG. 9 shows alpha power at 12 Hz over the parietal lobe, demonstrating how the stimulus can be used in conjunction with high-level perceptual and cognitive measures.

Example 3

Figure 10:
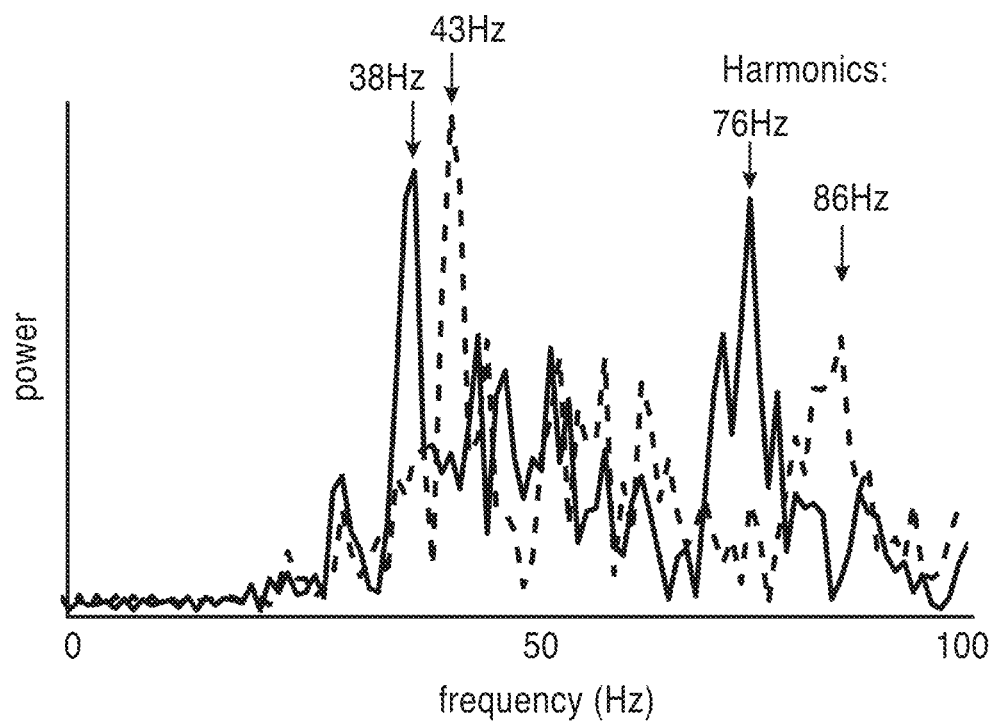
FIG. 10 is a graph that shows ASSRs from an ancillary demonstration where two independent chirp-speech signals were presented dichotically (simultaneously with different signal in each ear).

Auditory Steady State Response (ASSR) responses for simultaneous chirp-speech stimulus signals were taken to characterize how well speech information is passed from lower to higher levels in the auditory system. FIG. 10 shows ASSRs from an ancillary demonstration where two independent chirp-speech signals were presented dichotically (simultaneously with different signal in each ear). In this case the pitches and therefore chirp rates were different between ears: 38 Hz and 43 Hz. Chirps and speech were frequency-multiplexed in opposing bands between the ears, such that a given band contained chirps for one ear and speech for the other.

From the discussion above it will be appreciated that the technology described herein can be embodied in various ways, including the following:

1. A method for generating synthetic sound-speech stimuli for analyzing electrical brain activity, the method comprising: (a) providing at least one speech corpus having a plurality of utterances; (b) selecting a train of synthetic sounds; and (c) multiplexing the train of synthetic sounds with the speech corpus; (d) wherein the synthetic sounds are temporally aligned with the utterances of the speech corpus.

2. The method of any preceding embodiment, further comprising: flattening speech corpus pitch to an approximately constant value; and temporally shifting glottal pulses of the speech corpus; wherein voicing phase is kept consistent within and across speech utterances.

3. The method of any preceding embodiment, wherein the pitch constant value is approximately 82 Hz, the lower limit of a male voice.

4. The method of any preceding embodiment, wherein times of pitch-flattened glottal pulses are shifted by approximately half a pitch period or less.

5. The method of any preceding embodiment, wherein the speech corpus is a common clinical speech corpus selected from the group consisting of HINT, QuickSIN, Synthetic Sentence Identification test and the Harvard/IEEE (1969) speech corpus.

6. The method of any preceding embodiment, wherein the synthetic sound is a non-speech sound selected from the group consisting of chirps, clicks, tones, tone-complexes, and amplitude-modulated noise bursts.

7. The method of any preceding embodiment, wherein the synthetic sound is an isochronous or non-isochronous chirp train.

8. The method of any preceding embodiment, wherein the synthetic sound is an isochronous 41 Hz series of cochlear chirps.

9. The method of any preceding embodiment claim 1, wherein the frequency multiplexing further comprises: splitting a frequency axis into alternating bands of speech and synthetic sound; wherein disruptive interactions between the speech and synthetic sounds along the basilar membrane and in their neural representations are minimized.

10. The method of any preceding embodiment, further comprising: temporally aligning the synthetic sounds to consonant plosives and glottal pulses of the speech corpus.

11. A method for analyzing electrical brain activity from auditory stimuli, the method comprising: (a) providing one or more frequency-multiplexed synthetic sound-speech stimuli; (b) presenting at least one stimulus to a test subject; and (c) evaluating detected electrophysiological responses of the test subject to the applied stimulus.

12. The method of any preceding embodiment, further comprising: incorporating the frequency-multiplexed synthetic sound-speech stimuli in a neural or behavioral test system that utilizes an auditory stimuli.

13. The method of any preceding embodiment, wherein the test system is a test selected from the group of tests consisting of the Auditory Brainstem Response (ABR), Middle Latency Response (MLR), Auditory Steady State Response (ASSR), and Long Latency Response (LLR).

14. The method of any preceding embodiment, wherein the frequency-multiplexed synthetic sound-speech stimuli is provided from a library of stimuli.

15. The method of any preceding embodiment, wherein the frequency-multiplexed synthetic sound-speech stimuli is generated with the steps comprising: providing at least one speech corpus having a plurality of utterances; selecting a train of synthetic sounds; and multiplexing the train of synthetic sounds with the speech corpus to produce the stimuli; wherein the synthetic sounds are temporally aligned with the utterances of the speech corpus.

16. The method of any preceding embodiment, further comprising: flattening speech corpus pitch to an approximately constant value; and temporally shifting glottal pulses of the speech corpus; wherein voicing phase is kept consistent within and across speech utterances.

17. The method of any preceding embodiment, wherein the speech corpus is a common clinical speech corpus selected from the group consisting of HINT, QuickSIN, Synthetic Sentence Identification test and the Harvard/IEEE (1969) speech corpus.

18. The method of any preceding embodiment, wherein the synthetic sound is a non-speech sound selected from the group consisting of chirps, clicks, tones, tone-complexes, and amplitude-modulated noise bursts.

19. The method of any preceding embodiment, wherein the frequency multiplexing further comprises: splitting a frequency axis into alternating bands of speech and synthetic sound; wherein disruptive interactions between the speech and synthetic sounds along the basilar membrane and in their neural representations are minimized.

20. The method of any preceding embodiment, further comprising: temporally aligning the synthetic sounds to consonant plosives and glottal pulses of the speech corpus.

21. A system for detecting and analyzing electrical brain activity, comprising: (a) at least one detector; (b) a computer processor; and (c) a non-transitory computer-readable memory storing instructions executable by the computer processor; (d) wherein the instructions, when executed by the computer processor, perform steps comprising: (i) providing at least one speech corpus having a plurality of utterances; (ii) flattening speech corpus pitch to an approximately constant value; (iii) temporally shifting glottal pulses of the speech corpus; (iv) providing a train of synthetic sounds that evoke strong auditory system responses; (v) multiplexing the train of synthetic sounds with the speech corpus so that the synthetic sounds are temporally aligned with the utterances of the speech corpus to produce the stimuli; and (vi) detecting electrophysiological responses of a test subject to the applied stimulus with the detector.

22. The system of any preceding embodiment, wherein the detector is selected from the group of detectors consisting of electroencephalography EEG, magnetoencephalography MEG, electrocorticography ECoG, and cochlear implant telemetry.

23. The system of any preceding embodiment, wherein the speech corpus is a common clinical speech corpus selected from the group consisting of HINT, QuickSIN, Synthetic Sentence Identification test and the Harvard/IEEE (1969) speech corpus.

24. The system of any preceding embodiment, wherein the synthetic sound is a non-speech sound selected from the group consisting of chirps, clicks, tones, tone-complexes, and amplitude-modulated noise bursts.

25. The system of any preceding embodiment, the instructions further comprising: temporally aligning the synthetic sounds to consonant plosives and glottal pulses of the speech corpus.

Embodiments of the present technology may be described with reference to flowchart illustrations of methods and systems, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

```
% CHEECH_STIMGEN.M (MATLAB function)
function [signal,cuelat,cuelabl]=cheech_stimgen(outputPath,f0,filterSpeechBands,
filterChirpBands,stimcue,cueplus,invert)
% CHEECH_STIMGEN.M
% Function to generate chirp-speech multiplexed stimulus designed to evoke
% neural activity from various processing levels along the ascending
% human auditory pathway, including the Auditory Brainstem
% Response (ABR), Middle Latency Response (MLR), Auditory Steady State
% Response (ASSR), and Long Latency Response (LLR).
% Inputs:
%                       outputPath = output path, with trailing slash;
%                       f0 = fundamental for checking voicing phase. This MUST be
%                                    confirmed same as what is hardcoded in
%                                    FlatIntonationSynthesizer.psc. Default =82;
%                       filterSpeechBands = [250 500; 1000 2000; 4000 0]; % set
%                                    speech filter STOP bands;use '0' for low or high-pass
%                       filterChirpBands = [0 250; 500 1000; 2000 4000]; % chirp
%                                    filter STOP bands; use '0' for low or high-pass
%                       stimcue = code used as wav cue at stim onset; default = 10, to %
%                                    indicate e.g. stimulus or experimental conditions in %
%                                    the eeg file
%                       cueplus = 0; %additive index for disambiguating wave cues, as
%                                    when cue numbering different for right vs left
%                                    ear; e.g. 0 for left ear(cues 99, 100, etc);
%                                    100 for right ear (cues 199, 200, etc).
%                       invert = 0; %flag to invert entire waveform before writing.
%                                    0 = no (default) or 1 = yes
%
% This function makes use of several additional resources:
% -The Harvard/IEEE (1969)speech corpus, spoken by a male actor
% -The PRAAT acoustic analysis software package (www.praat.org)
% -Chirp auditory stimuli from Elberling, Callo, & Don 2010, part of the
%   Auditory Modelling Toolbox (http://amtoolbox.sourceforge.net/doc/)
% - filters from the ERPlab toolbox ca. 2013 (filterb.m, filter_tf.m)
%                                    (http://erpinfo.org/erplab); IIR Butterworth zero phase
%                                    using matlab's filtfilt.m
%% defaults
if ~exist('stimcue','var')
    stimcue = 10;
end
if ~exist('cueplus','var')
    cueplus = 0;
end
if ~exist('invert','var')
    invert = 0;
end
catNum = 50; % specify number of sentences to concatenate
gmin=0.050; % minimum leading &/or trailing silence between sentences when
            concatenated, in sec
thr = 0.01; % speech envelope threshold, used for identifying and
            demarcating silences
```

TABLE 1-continued

```
voiceFilt = [20 1000]; % in Hz. bandpass filter to create envelope used for
               identifying voicing by power (and avoid fricatives)
voiceThresh = 0.015% threshold to identify voiced periods (from power in
               lowpass filtered speech)
minimumChirpCycles = 4; % minimum voiced duration in order to add chirps
ampchirp = 0.15% normalized chirp amplitude to match speech power in corpus
plotflag=0;
    %% First Concatenate sentences (these recordings are at 22050 Hz sampling
rate)
corpusPath= 'C:\IEEE_male\';
fileList = dir([corpusPath '*.wav']); % get a list of files
for stim=1:1 % (loop in case you wish to batch process many stimuli)
    signal = [ ];
    for sentNum = 1:catNum
        fileName = [corpusPath fileList(sentNum+((stim+−1)*catNum)).name];
        [trimSentence,Fs,gap] = silence_trim(fileName,thr,gmin,plotflag);
        signal=[signal ; trimSentence]; % Concatenate trimmed sentences
    end
    wavwrite(signal,Fs,[ outputPath 'stim' num2str(stim) '.wav']);
    disp( [ outputPath 'stim' num2str(stim) '.wav'] )
end
%% Now 'flatten' speech pitch with PRAAT
% wav files must be in outputPath
% FILES WILL BE OVERWRITTEN WITH FLATTENED VERSIONS
% both pratcon.exe and the FlatIntonationSynthesizer.psc script must be
% at this location
cd(outputPath);
% now call PRAATCON, which will synthesize glottal pulses at the frequency
% specified in FlatIntonationSynthesizer.psc (currently 82Hz)
disp('Note, the Praat flattening script overwrites the originals; also it is currently
hardcoded for frequency - check that you have the right one');
[status,result]=system([outputPath 'praatcon FlatIntonationSynthesizer.psc'])
fo stimNum = 1:1    % loop for batching many stims
% Process the speech signal
flatSpeechUnfiltered = ['stim' num2str(stimNum) '.wav'];
[flatSpeech,Fs,Nbits]=wavread(flatSpeechUnfiltered);
disp('Lowpass filtering to identify voiced periods by their power (and avoid
fricatives).')
flatSpeechlow = filterb(flatSpeech,[0 voiceFilt(1); voiceFilt(2) 0], Fs, 10);
y = abs(hilbert(flatSpeechlow));
tempenv = filterb(y,[0 0.0001; 40 0], Fs, 4);
figure, plot(tempenv), title('tempenv')
% identify phase of synthesized glottal pulses so chirps can be aligned
[phaseoff,timeoff,envoice,envhist] = voicing_phase(flatSpeech,Fs,f0,plotflag);
sampleoff = round( Fs * timeoff) ; % phase offset in samples method 2
% filter the flattened speech
filterorder = 20;
flatSpeech = filterb(flatSpeech,filterSpeechBands, Fs, filterorder); % filter
    %% generate the chirp Train
chirpFreq = f0/2; % in Hz; in this case half the voiced fundamental
chirpInterval=Fs/chirpFreq;
repeats = ceil(length(flatSpeech) / chirpInterval ); % Number of chirps per burst
constantOffset = 0; % this value is used to precisely align every chirp to the
speech glottal pulses
chirpPath = 'C:\chirps\';
chirpLength = 343; % in this case actual chirp waveforms are just first 343
samples (16ms @ 22050Hz)
[chirp1,FsChirp,nBits] = wavread([chirpPath 'chirp1_22kHz.wav']); % sample is
30ms long at 22050 kHz.
if Fs~=FsChirp
    error('Sampling rate of sounds and chirp wav are different')
end
chirp1 = chirp1(1:chirpLength);
chirpIndices = round (((0:repeats)*chirpInterval) + 1 );
chirpTrain = zeros(chirpIndices(end),1);
for chirpNum = 2:repeats+1
    chirpTrain(chirpIndices(chirpNum)−(chirpLength−1):chirpIndices(chirpNum)) =
chirp1;
end
leadingSilence = 0.005; % in seconds; this is just to give some onset time so
                        % EEG acquisition software doesn't miss the first cue
leadingSilence = zeros(Fs*leadingSilence,1); % in samples
% Shift the chirp train to align with glottal pulses
chirpTrain = [leadingSilence; zeros(sampleoff + constantOffset ,1); chirpTrain];
chirpIndices = chirpIndices + length(leadingSilence) + sampleoff + constantOffset;
chirpTrain=ampchirp .* chirpTrain(1:length(flatSpeech)); % set the
%                             chirpTrain amplitude and shorten length to match voice sample
%                             also shift speech signal to play nice with EEG acquisition
flatSpeech = [ leadingSilence ; flatSpeech];
```

TABLE 1-continued

```
% filter the chirp train:
filterorder = 20;
chirpTrain = filterb(chirpTrain,filterChirpBands, Fs, filterorder);
chirpTrainForVoice = zeros(length(flatSpeech),1);    % generate a blank chirp
                                                    % train for later
%%% now insert full chirps only during voiced segments
V=tempenv;
V(V<=voiceThresh) = 0; V(V>0) = 1;
D = diff([0,V',0]);                        %find onsets and offsets of voiced segments
voiceStart = find(D == 1);
voiceStop = find(D == -1) - 1;
figure; hold on
plot(tempenv,'k');plot(flatSpeech)
cuelat = [ ]; cuelat(1) = 0;                        % needed for writing the trigger cues into
                                                    % wav files, to indicate chirp times to eeg
                                                    % acquisition software
cuelabl = [ ]; cuelabl{1} = num2str(stimcue);
for voicedSegment=1:length(voiceStart)
        chirpIndicesForVoice = find(chirpIndices > voiceStart(voicedSegment) &
                        chirpIndices < voiceStop(voicedSegment) );
    if length(chirpIndicesForVoice) > minimumChirpCycles &&
            ~isempty(chirpIndicesForVoice)
        chirpTrainForVoice( chirpIndices(chirpIndicesForVoice(1)-
                        1):chirpIndices(chirpIndicesForVoice(1)) )= ...
        chirpTrain(chirpIndices(chirpIndicesForVoice(1)-
                        1):chirpIndices(chirpIndicesForVoice(1)));
        % drop the second chirp in order to extract Middle Latency Response
        chirpTrainForVoice(chirpIndices(chirpIndicesForVoice(2)):
                        chirpIndices(chirpIndicesForVoice(end)) )= ...
                        chirpTrain(chirpIndices(chirpIndicesForVoice(2)):
                        chirpIndices(chirpIndicesForVoice(end)));
        cueNum = 1;
        cuelat(end+1)= chirpIndices(chirpIndicesForVoice(cueNum));
                        % in samples
        cuelabl{end+1}= num2str( (cueNum-1) + 100 + cueplus);
                        % cue label (text string)
        % (drop the second chirp in order to extract Middle Latency Response)
        for cueNum = 3:length(chirpIndicesForVoice)
            cuelat(end+1)= chirpIndices(chirpIndicesForVoice(cueNum));
                        % in samples
            cuelabl{end+1}= num2str( (cueNum-1) + 100 + cueplus);
                        % cue label (text string)
        end
                % give last chirp in voiced epoch special label
        cuelabl{end}= num2str(99 + cueplus) ; % cue label (text string)
    end
    end
%%% check range of the trigger cues
if max(cellfun(@str2num, cuelabl))>255 | min(cellfun(@str2num, cuelabl))<0
    warning('you have wav cues outside the range [0,255]! These may not work
            to send parallel port triggers')
end
% combine (MULTIPLEXED) speech and chirps
signal = flatSpeech+chirpTrainForVoice;
% phase invert if desired
if invert
    signal = -signal;
end
% and convert multiplexed stimulus to mono or stereo
channels = 0; % 0=mono, 1=left, 2=right, 3=binaural
switch channels
    case 0 % mono
        %(do nothing)
    case 1 % left chan
        signal = [signal zeros(length(signal),1)];
    case 2 % right chan
        signal = [zeros(length(signal),1) signal];
    case 3 % both chans
        signal = [signal signal];
end
    % finally, write the sound file and add trigger event cues
wavwrite(signal,Fs,[outputPath flatSpeechUnfiltered(1:end-4)
                        'Multiplex.wav'])
            %must write the file first *before* adding trigger cues
addWavCue(outputPath,[flatSpeechUnfiltered(1:end-4)
            'Multiplex.wav'],cuelat,cuelabl,[flatSpeechUnfiltered(1:end-4)
            'MultiplexCUED.wav']) % adds cues info to a metadata block in wav file
end % stimNum
PRAAT FLAT INTONATION SYNTHESIZER

```

TABLE 1-continued

```
# Resynthesizes all the sound files in the
# specified directory to have flat pitch
# of the specified frequency. Files are
# saved in a specified directory.

#############################
sound_directory$ = "c:\temp\"
sound_file_extension$ = ".wav"
end_directory$ = "c:\temp\"
resynthesis_pitch = 82 #for our demonstration, 82Hz
# Here, you make a listing of all the sound files in a directory.
Create Strings as file list... list 'sound_directory$'*'sound_file_extension$'
numberOfFiles = Get number of strings
for ifile to numberOfFiles
filename$ = Get string... ifile
# A sound file is opened from the listing:
Read from file... 'sound_directory$''filename$'
sound_one$ = selected$ ("Sound")
To Manipulation... 0.01 60 400
# Create a new pitch tier with the flat pitch:
select Sound 'sound_one$'
start = Get start time
end = Get end time
Create PitchTier... 'sound_one$' start end
Add point... start resynthesis_pitch
Add point... end resynthesis_pitch
# Combine and save the resulting file:
select Manipulation 'sound_one$'
plus PitchTier 'sound_one$'
Replace pitch tier
select Manipulation 'sound_one$'
Get resynthesis (PSOLA)
Write to WAV file... 'end_directory$''filename$'
select Sound 'sound_one$'
plus Manipulation 'sound_one$'
plus PitchTier 'sound_one$'
Remove
select Strings list
endfor
select all
Remove
```

What is claimed is:

1. A method for analyzing electrical brain activity from auditory stimuli, the method comprising:
   (a) providing one or more frequency-multiplexed synthetic sound-speech stimuli, wherein the stimuli comprise at least one speech corpus that is multiplexed with a train of synthetic sounds;
   (b) presenting at least one stimulus from an audio system to a test subject;
   (c) detecting an electrophysiological response from the test subject to the presented stimulus; and
   (d) evaluating the detected electrophysiological response of the test subject.

2. The method as recited in claim 1, further comprising: incorporating the frequency-multiplexed synthetic sound-speech stimuli in a neural or behavioral test system that utilizes auditory stimuli.

3. The method as recited in claim 2, wherein said test system is a test selected from the group of tests consisting of the Auditory Brainstem Response (ABR), Middle Latency Response (MLR), Auditory Steady State Response (ASSR), and Long Latency Response (LLR).

4. The method as recited in claim 1, wherein said one or more frequency-multiplexed synthetic sound-speech stimuli are provided from a library of stimuli.

5. The method as recited in claim 1, wherein said one or more frequency-multiplexed synthetic sound-speech stimuli are generated with the steps comprising:
   providing at least one speech corpus having a plurality of utterances;
   selecting a train of synthetic sounds; and
   multiplexing the train of synthetic sounds with the speech corpus to produce the stimuli;
   wherein the synthetic sounds are temporally aligned with the utterances of the speech corpus.

6. The method as recited in claim 5, further comprising:
   flattening speech corpus pitch to an approximately constant value; and
   temporally shifting glottal pulses of the speech corpus;
   wherein voicing phase is kept consistent within and across speech utterances.

7. The method as recited in claim 6, wherein the speech corpus pitch is flattened to a constant value of approximately 82 Hz, the lower limit of a male voice.

8. The method as recited in claim 6, wherein times of pitch-flattened glottal pulses are shifted by approximately half a pitch period or less.

9. The method as recited in claim 5, wherein the speech corpus is a common clinical speech corpus selected from the group consisting of HINT, QuickSIN, Synthetic Sentence Identification test and the Harvard/IEEE (1969) speech corpus.

10. The method as recited in claim 5, wherein the synthetic sound is a non-speech sound selected from the group consisting of chirps, clicks, tones, tone-complexes, and amplitude-modulated noise bursts.

11. The method as recited in claim 5, wherein the frequency multiplexing further comprises:
   splitting a frequency axis into alternating bands of speech and synthetic sound;

wherein disruptive interactions between the speech and synthetic sounds along the basilar membrane and in their neural representations are minimized.

12. The method as recited in claim 5, further comprising: temporally aligning said synthetic sounds to consonant plosives and glottal pulses of the speech corpus.

13. The method as recited in claim 5, wherein the synthetic sound is an isochronous or non-isochronous chirp train.

14. The method as recited in claim 5, wherein the synthetic sound is an isochronous 41 Hz series of cochlear chirps.

15. A method for analyzing electrical brain activity from auditory stimuli, the method comprising:
(a) providing one or more frequency-multiplexed synthetic sound-speech stimuli, wherein the stimuli comprise at least one speech corpus that is multiplexed with a train of synthetic sounds such that the stimuli comprise a frequency axis split into two or more bands of speech and synthetic sound;
(b) presenting at least one stimulus from an audio system to a test subject;
(c) detecting an electrophysiological response of the test subject to the presented stimulus; and
(d) evaluating the detected electrophysiological response of the test subject.

16. The method as recited in claim 15, wherein the speech corpus is a common clinical speech corpus selected from the group consisting of HINT, QuickSIN, Synthetic Sentence Identification test and the Harvard/IEEE (1969) speech corpus.

17. The method as recited in claim 15, wherein the speech corpus is a speech utterance.

18. The method as recited in claim 15, wherein the synthetic sound is a non-speech sound selected from the group consisting of chirps, clicks, tones, tone-complexes, and amplitude-modulated noise bursts.

19. The method as recited in claim 15, wherein the synthetic sound is an isochronous or non-isochronous chirp train.

20. The method as recited in claim 15, wherein said one or more frequency-multiplexed synthetic sound-speech stimuli are provided from a library of stimuli.

* * * * *